United States Patent
Campbell et al.

(10) Patent No.: US 7,449,596 B2
(45) Date of Patent: Nov. 11, 2008

(54) METHOD OF MAKING A SYNTHETIC PETROLEUM SULFONATE

(75) Inventors: Curt B. Campbell, Hercules, CA (US); Thomas V. Harris, Benicia, CA (US); Gilles Sinquin, Saint Martin du Manoir (FR)

(73) Assignee: Chevron Oronite Company LLC, San Ramon, CA (US)

( * ) Notice: Subject to any disclaimer, the term of this patent is extended or adjusted under 35 U.S.C. 154(b) by 0 days.

(21) Appl. No.: 11/316,106

(22) Filed: Dec. 21, 2005

(65) Prior Publication Data

US 2007/0142665 A1  Jun. 21, 2007

(51) Int. Cl.
*C07C 309/31* (2006.01)

(52) U.S. Cl. .......................................... 562/94; 562/33

(58) Field of Classification Search .................. 562/33, 562/94
See application file for complete search history.

(56) References Cited

U.S. PATENT DOCUMENTS

| | | | | |
|---|---|---|---|---|
| 3,188,360 | A * | 6/1965 | Gudelis | 585/533 |
| 3,875,253 | A * | 4/1975 | Huang | 585/660 |
| 4,503,277 | A | 3/1985 | Himes | |
| 4,873,025 | A * | 10/1989 | Bolsman | 562/91 |
| 5,282,858 | A | 2/1994 | Bisch et al. | |
| 5,731,101 | A | 3/1998 | Sherif et al. | |
| 5,824,832 | A * | 10/1998 | Sherif et al. | 585/455 |
| 5,994,602 | A * | 11/1999 | Abdul-Sada et al. | 585/457 |
| 2004/0010161 | A1 * | 1/2004 | Maas et al. | 562/94 |

FOREIGN PATENT DOCUMENTS

WO   WO 98/50153   11/1998

OTHER PUBLICATIONS

Dermot J. Collins et al. Isomerization And Disproportionation Of Xylenes With An Aluminum Chloride Catalyst, Applied Catalysis, 8 (1993) 273-288, 1983 Elsevier Science Publisher B.V.

Christopher J. Adams, et al., Friedel-Crafts Reactions In Room Temperature Ionic Liquids, School of Chemistry, The Queen's University of Belfast, Stranmillis Road, Belfast, Northern Ireland, UK BT9 5AG, Unilever Research Laboratories, Port Sunlight, Bebington, Wirral, England, UK L63 3JW, 1998 Chem. Comm.

Jeffrey A. Boon et al., Friedel-Crafts Reactions In Ambient-Tempature Molten Salts, The Frank J. Seiler Research Laboratory, United States Air Force Academy, Colorado Springs, Colorado 80840-6525, J. Org Chem. 1986, 51, 480-483., 1986 American Chemical Society.

Jeffrey A. Boon, Joseph A. Levisky, J. Floyd Pflug and John S. Wilkes, Friedel-Crafts Reactions in Ambient-Temperature Molten Salts, J. Org. Chemistry, 1986, 51, 480-483, American Chemical Society, Colorado Springs, Colorado.

* cited by examiner

*Primary Examiner*—Peter G O'Sullivan
(74) *Attorney, Agent, or Firm*—Josetta I. Jones

(57) ABSTRACT

A process for preparing a synthetic petroleum sulfonate comprising (a) reacting at least one aromatic compound with a mixture of olefins selected from olefins having from about 8 to about 100 carbon atoms, in the presence of an acidic ionic liquid catalyst, wherein the resulting product comprises at least about 50 weight percent of a 1,2,4 tri-substituted aromatic compound or a 1,2,3 tri-substituted aromatic compound or mixtures thereof; (b) reacting the product of (a) with sulfur trioxide, which has been diluted with air; and (c) neutralizing the product of (b) with an alkali or alkaline earth metal hydroxide.

29 Claims, No Drawings

METHOD OF MAKING A SYNTHETIC PETROLEUM SULFONATE

FIELD OF THE INVENTION

The present invention is directed to a method of making a synthetic petroleum sulfonate that is derived by sulfonating an alkylated aromatic compound made from a process of alkylating an aromatic compound with a mixture of olefins selected from olefins having from about 8 to about 100 carbon atoms in the presence of acidic ionic liquids. These sulfonates exhibit superior performance as enhanced oil recovery surfactants.

BACKGROUND OF THE INVENTION

It is well known to catalyze the alkylation of aromatics with a variety of Lewis or Bronsted acid catalysts. Typical commercial catalysts include phosphoric acid/kieselguhr, aluminum halides, boron trifluoride, antimony chloride, stannic chloride, zinc chloride, onium poly(hydrogen fluoride), and hydrogen fluoride. Alkylation with lower molecular weight olefins, such as propylene, can be carried out in the liquid or vapor phase. For alkylations with higher olefins, such as C16+ olefins, the alkylations are done in the liquid phase, usually in the presence of hydrogen fluoride. Alkylation of benzene with higher olefins is especially difficult, and requires hydrogen fluoride treatment. Such a process is disclosed by Himes in U.S. Pat. No. 4,503,277, entitled "HF Regeneration in Aromatic Hydrocarbon Alkylation Process," which is hereby incorporated by reference for all purposes.

The use of acids, such as hydrogen fluoride, is extremely corrosive, thus requiring special handling and equipment. Also, the use of these acids might involve environmental problems. Another problem is that the use of these acids gives less desirable control on the precise chemical composition.

DESCRIPTION OF THE RELATED ART

Abdul-Sada et al., U.S. Pat. No. 5,994,602 discloses a process for the alkylation of aromatics by reacting an aromatic hydrocarbon with an olefin in the presence of an ionic liquid comprising (a) a compound of the formula $R_nMX_{3-n}$ wherein R is a C1-C6 alkyl radical, M is aluminum or gallium, X is a halogen atom and n is 0, 1 or 2 and, (b) a hydrocarbyl substituted imidazolium halide or a hydrocarbyl substituted pyridinium halide wherein at least one of the said hydrocarbyl substituents in the imidazolium halide is an alkyl group having 1-18 carbon atoms.

Sherif et al., U.S. Pat. No. 5,824,832 discloses a low temperature molten ionic liquid composition comprising a mixture of a metal halide and an alkyl-containing amine hydrohalide salt that can be used in linear alkylbenzene formation.

Sherif et al., U.S. Pat. No. 5,731,101 discloses a low temperature molten ionic liquid composition comprising a mixture of a metal halide and an alkyl-containing amine hydrohalide salt is described which is useful as a catalyst and a solvent in alkylation, arylation, and polymerization reactions or as an electrolyte for batteries. Steichen et al., WO 98/50153 discloses a process related to in-situ formation of an ionic liquid catalyst for use in an ionic liquid-catalyzed chemical reaction. The in-situ formed liquid catalyst is applicable to a variety of ionic-liquid catalyzed chemical reactions including, for example, the alkylation of a benzene or phenol reagent, the oligomerization of an olefin, or the alkylation of a paraffin. In the most preferred alkylation reaction, the invention relates to the catalytic alkylation of an aromatic molecule with a suitable alkylating reagent (e.g., a C2 to C20, such as C4 to C14 olefin or a halogenated alkane of similar chain length, using, as the catalyst, a composition which is liquid at low temperatures and which is formed in situ.

SUMMARY OF THE INVENTION

In its broadest embodiment, a process for preparing a synthetic petroleum sulfonate comprising
(a) reacting at least one aromatic compound with a mixture of olefins selected from olefins having from about 8 to about 100 carbon atoms, in the presence of an acidic ionic liquid catalyst, wherein the resulting product comprises at least about 50 weight percent of a 1, 2, 4 tri-substituted aromatic compound or a 1, 2, 3 tri-substituted aromatic compound or mixtures thereof;
(b) reacting the product of (a) with sulfuir trioxide, which has been diluted with air; and
(c) neutralizing the product of (b) with an alkali or alkaline earth metal hydroxide.

Accordingly, the present invention relates to a process for preparing a sulfonated alkylated aromatic.

DETAILED DESCRIPTION OF THE INVENTION

While the invention is susceptible to various modifications and alternative forms, specific embodiments thereof are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

Definitions

Olefins—The term "olefins" refers to a class of unsaturated aliphatic hydrocarbons having one or more carbon-carbon double bonds, obtained by a number of processes. Those containing one double bond are called mono-alkenes, and those with two double bonds are called dienes, alkyldienes, or diolefins. Alpha olefins are particularly reactive because the double bond is between the first and second carbons. Examples are 1-octene and 1-octadecene, which are used as the starting point for medium-biodegradable surfactants. Linear and branched olefins are also included in the definition of olefins.

Linear Olefins—The term "linear olefins," which include normal alpha olefins and linear alpha olefins, refers to olefins which are straight chain, non-branched hydrocarbons with at least one carbon-carbon double bond present in the chain.

Double-Bond Isomerized linear Olefins—The term "double-bond isomerized linear olefins" refers to a class of linear olefins comprising more than 5% of olefins in which the carbon-carbon double bond is not terminal (i.e., the double bond is not located between the first and second carbon atoms of the chain).

Partially Branched Linear Olefins—The term "partially branched linear olefins" refers to a class of linear olefins comprising less than one alkyl branch per straight chain containing the double bond, wherein the alkyl branch may be a methyl group or higher. Partially branched linear olefins may also contain double-bond isomerized olefin.

Branched Olefins—The term "branched olefins" refers to a class of olefins comprising one or more alkyl branches per linear straight chain containing the double bond, wherein the alkyl branch may be a methyl group or higher.

$C_{12}$-$C_{30}^+$ Normal Alpha Olefins—This term defines a fraction of normal alpha olefins wherein the carbon numbers below 12 have been removed by distillation or other fractionation methods.

One embodiment of the present invention is a process for preparing an alkylated aromatic compound, wherein said process comprises reacting at least one aromatic compound with a mixture of olefins selected from olefins having from about 8 carbon atoms to about 100 carbon atoms, in the presence of an acidic ionic liquid catalyst, wherein the resulting product comprises at least about 50 weight percent of a 1,2,4 tri-substituted aromatic compound or a 1,2,3 tri-substituted aromatic compound or mixtures thereof.

Aromatic Compound

At least one aromatic compound or a mixture of aromatic compounds may be used for the alkylation reaction in the present invention. Preferably the at least one aromatic compound or the aromatic compound mixture comprises at least one of monocyclic aromatics, such as benzene, toluene, xylene, cumene or mixtures thereof. The at least one aromatic compound or aromatic compound mixture may also comprise bi-cyclic and poly-cyclic aromatic compounds, such as naphthalenes. More preferably, the at least one aromatic compound or aromatic compound mixture is xylene, including all isomers (i.e., meta-, ortho- and para-), a raffinate of xylene isomerization, and mixtures thereof. Most preferably, the at least one aromatic compound is ortho-xylene.

Sources of Aromatic Compound

The at least one aromatic compound or the mixture of aromatic compounds employed in the present invention is prepared by methods that are well known in the art.

Olefins

Sources of Olefins

The olefins employed in this invention may be linear, isomerized linear, branched or partially branched linear. The olefin may be a mixture of linear olefins, a mixture of isomerized linear olefins, a mixture of branched olefins, a mixture of partially branched linear or a mixture of any of the foregoing.

The olefins may be derived from a variety of sources. Such sources include the normal alpha olefins, linear alpha olefins, isomerized linear alpha olefins, dimerized and oligomerized olefins, and olefins derived from olefin metathesis. Another source from which the olefins may be derived is through cracking of petroleum or Fischer-Tropsch wax. The Fischer-Tropsch wax may be hydrotreated prior to cracking. Other commercial sources include olefins derived from paraffin dehydrogenation and oligomerization of ethylene and other olefins, methanol-to-olefin processes (methanol cracker) and the like.

The olefins may also be substituted with other functional groups, such as hydroxy groups, carboxylic acid groups, heteroatoms, and the like, provided that such groups do not react with the acidic ionic liquid catalyst.

The mixture of olefins is selected from olefins with carbon numbers ranging from about 8 carbon atoms to about 100 carbon atoms. Preferably, the mixture of olefins is selected from olefins with carbon numbers ranging from about 10 to about 80 carbon atoms, more preferred from about 14 to about 60 carbon atoms.

In another embodiment, preferably, the mixture of olefins is selected from linear alpha olefins or isomerized olefins containing from about 8 to about 100 carbon atoms. More preferably, the mixture of olefins is selected from linear alpha olefins or isomerized olefins containing from about 10 to about 80 carbon atoms. Most preferably, the mixture of olefins is selected from linear alpha olefins or isomerized olefins containing from about 14 to about 60 carbon atoms.

Furthermore, in a preferred embodiment, the mixture of olefins contains a distribution of carbon atoms that comprise from about 40 to about 90 percent $C_{12}$ to $C_{20}$ and from about 4 percent to about 15 percent $C_{32}$ to $C_{58}$. More preferably, the distribution of carbon atoms comprises from about 50 to about 80 percent $C_{12}$ to $C_{20}$ and from about 4 percent to about 15 percent $C_{32}$ to $C_{58}$.

The mixture of branched olefins is preferably selected from polyolefins which may be derived from $C_3$ or higher monoolefins (i.e., propylene oligomers, butylenes oligomers, or co-oligomers etc.). Preferably, the mixture of branched olefins is either propylene oligomers or butylenes oligomers or mixtures thereof.

Normal Alpha Olefins

Preferably, the mixture of linear olefins that may be used for the alkylation reaction is a mixture of normal alpha olefins selected from olefins having from about 8 to about 100 carbon atoms per molecule. More preferably the normal alpha olefin mixture is selected from olefins having from about 10 to about 80 carbon atoms per molecule. Most preferably, the normal alpha olefin mixture is selected from olefins having from about 12 to about 60 carbon atoms per molecule. An especially preferred range is from about 14 to about 60.

In one embodiment of the present invention, the normal alpha olefins are isomerized using at least one of two types of acidic catalysts, solid or liquid. A solid catalyst preferably has at least one metal oxide and an average pore size of less than 5.5 angstroms. More preferably, the solid catalyst is a molecular sieve with a one-dimensional pore system, such as SM-3, MAPO-11, SAPO-11, SSZ-32, ZSM-23, MAPO-39, SAPO-39, ZSM-22 or SSZ-20. Other possible acidic solid catalysts useful for isomerization include ZSM-35, SUZ-4, NU-23, NU-87 and natural or synthetic ferrierites. These molecular sieves are well known in the art and are discussed in Rosemarie Szostak's Handbook of Molecular Sieves (New York, Van Nostrand Reinhold, 1992) which is herein incorporated by reference for all purposes. A liquid type of isomerization catalyst that can be used is iron pentacarbony ($Fe(CO)_5$).

The process for isomerization of normal alpha olefins may be carried out in batch or continuous mode. The process temperatures may range from about 50° C. to about 250° C. In the batch mode, a typical method used is a stirred autoclave or glass flask, which may be heated to the desired reaction temperature. A continuous process is most efficiently carried out in a fixed bed process. Space rates in a fixed bed process can range from 0.1 to 10 or more weight hourly space velocity.

In a fixed bed process, the isomerization catalyst is charged to the reactor and activated or dried at a temperature of at least 150° C. under vacuum or flowing inert, dry gas. After activation, the temperature of the isomerization catalyst is adjusted to the desired reaction temperature and a flow of the olefin is introduced into the reactor. The reactor effluent containing the partially-branched, isomerized olefins is collected. The resulting partially-branched, isomerized olefins contain a different olefin distribution (i.e., alpha olefin, beta olefin; internal olefin, tri-substituted olefin, and vinylidene olefin) and branching content that the unisomerized olefin and conditions are selected in order to obtain the desired olefin distribution and the degree of branching.

Acidic Ionic Liquid Catalyst

The acidic ionic liquid catalyst is composed of two components which form a complex. The first component of the catalyst will typically comprise a compound selected from the group consisting of aluminum halide, alkyl aluminum halide, gallium halide, and alkyl gallium halide. Especially preferred for the first component is aluminum halide or alkyl aluminum halide. In particular, aluminum trichloride may be used as the first component for preparing the catalyst used in practicing the present invention.

The second component making up the ionic liquid catalyst is an organic salt or mixture of salts. These salts may be characterized by the general formula $Q^+A^-$, wherein $Q^+$ is an ammonium, phosphonium, or sulfonium cation and $A^-$ is a negatively charged ion such as $Cl^-$, $Br^-$, $ClO_4^-$, $NO_3^-$, $BF_4^-$, $BCL_4^-$, $PF_6^-$, $SbF_6^-$. $AlCl_4^-$, $ArF_6^-$, $TaF_6^-$, $CuCl_2^-$, $FeCl_3^-$, $SO_3CF_3^-$, $SO_3C_7^-$, and 3-sulfurtrioxyphenyl. Preferred for use as the second component are those quaternary ammonium halides containing one or more alkyl moieties having from about 1 to about 9 carbon atoms, such as, for example, trimethylamine hydrochloride, methyltributylammonium, and 1-butylpyridinium, or hydrocarbyl substituted imidazolium halides, such as for example, 1-ethyl-3-methyl-imidazolium chloride.

The presence of the first component should give the ionic liquid a Lewis acidic character. Generally, the greater the mole ratio of the first component to the second component, the greater the acidity of the ionic liquid mixture. When aluminum trichloride and trimethylamine hydrochloride are used as the first and second components, respectively, of the acidic ionic liquid catalyst, they preferably will be present in a mole ratio of from greater than about 1:1 to about 2:1.

The alkylation process may be carried out in a batch or continuous process. The acidic ionic liquid catalyst may be recycled when used in a continuous process or batch process.

Process for Preparing Alkylated Aromatic Compound

In one embodiment of the present invention, the alkylation process is carried out by charging a hydrocarbon feed comprising an aromatic compound or a mixture of aromatic compounds, a mixture of olefin compounds and an acidic ionic liquid catalyst to a reaction zone in which agitation is maintained. The resulting mixture is held in the alkylation zone under alkylation conditions for a time sufficient to allow substantial conversion (i.e., at least 80 mole % of the olefin has reacted) of the olefin to aromatic alkylate. After desired time, the reaction mixture is removed from the alkylation zone and fed to a liquid-liquid separator to allow hydrocarbon products to separate from the acidic ionic liquid catalyst. The acidic ionic liquid catalyst is recycled to the reactor in a closed loop cycle. The hydrocarbon product is further treated to remove excess un-reacted aromatic compounds and optionally olefinic compounds from the desired alkylate product. The excess aromatic compounds are also recycled to the reactor.

Many types of reactor configurations may be used for the reactor zone. These include, but are not limited to, batch and continuous stirred tank reactors, reactor riser configurations, ebulating bed reactors, and other reactor configurations that are well known in the art. Many such reactors are known to those skilled in the art and are suitable for the alkylation reaction. Agitation is critical for the alkylation reaction and can be provided by rotating impellers, with or without baffles, static mixers, kinetic mixing in risers, or any other agitation devices that are well known in the art.

The alkylation process may be carried out at temperatures from about 0° C. to about 100° C. The process is carried out under sufficient pressure that a substantial portion of the feed components remain in the liquid phase. Typically, a pressure of 0 to 150 psig is satisfactory to maintain feed and products in the liquid phase.

The residence time in the reactor is a time that is sufficient to convert a substantial portion of the olefin to alkylate product. The time required is from about 30 seconds to about 30 minutes. A more precise residence time may be determined by those skilled in the art using batch stirred tank reactors to measure the kinetics of the alkylation process.

The at least one aromatic compound or mixture of aromatic compounds and the mixture of olefins may be injected separately into the reaction zone or may be mixed prior to injection. Both single and multiple reaction zones may be used with the injection of the aromatic compounds and the mixture of olefins into one, several, or all reaction zones. The reaction zones need not be maintained at the same process conditions.

The hydrocarbon feed for the alkylation process may comprise a mixture of aromatic compounds and a mixture olefins in which the molar ratio of aromatic compounds to olefins is from about 0.5:1 to about 50:1 or more. In the case where the molar ratio of aromatic compounds to olefin is >1.0, there is an excess amount of aromatic compounds present. Preferably an excess of aromatic compounds is used to increase reaction rate and improve product selectivity. When excess aromatic compounds are used, the excess un-reacted aromatic in the reactor effluent can be separated, e.g. by distillation, and recycled to the reactor.

One embodiment of the present invention is a continuous process with closed loop catalyst recycle. A hydrocarbon feed comprising aromatic compound(s) or a mixture of aromatic compounds and a mixture of olefin(s) is charged continuously by a and pumped to a reactor. Alternatively, the aromatic compound(s) and mixture of olefin(s) may be charged by separate lines and pumps to another line. At the beginning of the process fresh acidic ionic liquid catalyst is charged and pumped 20 to a reactor. The hydrocarbon feed and acidic ionic liquid catalyst are maintained in a reactor with agitation under alkylation process conditions for a sufficient time in order for a substantial amount of the mixture of olefins in the feed charge to react and form an aromatic alkylate compound. Pressure in the reactor is maintained by a backpressure valve. The effluent from the reactor is passed through the backpressure valve to a separator via a line. In the separator, the immiscible hydrocarbon and ionic liquid catalyst separate into two phases. As the acidic ionic liquid catalyst is more dense than the hydrocarbon phase, the acidic ionic liquid catalyst settles to the bottom of the separator. When a sufficient volume of acidic ionic liquid catalyst is available to fill a line and the bottom of the separator, the flow of fresh catalyst via a line is stopped and "used" or "recycled" catalyst is returned to the reactor from the separator via a line. The major portion of this process is thus operated under conditions of catalyst recycle, under which no fresh catalyst is added or only a small amount of make-up catalyst is added. The hydrocarbon product stream containing the aromatic alkylate compound and excess un-reacted aromatic is charged to a product separation section via a line. In product separation, excess aromatic compounds are distilled off and returned to the reactor, leaving a tri-substituted alkylated aromatic compound.

Tri-Substituted Alkylated Aromatic Compound

The product of the presently claimed invention is a tri-substituted alkylated aromatic compound. Preferably, the resulting product comprises at least about 50 weight percent of a 1, 2, 4 tri-substituted aromatic compound or a 1, 2, 3 tri-substituted aromatic compound or mixtures thereof. More preferably, the resulting product comprises at least about 80 weight percent, even mor preferably at least about 95 weight percent, of a 1, 2, 4 tri-substituted aromatic compound or a 1, 2, 3 tri-substituted aromatic compound or mixtures thereof. Most preferably, the resulting product comprises at least about 98 weight percent of a 1, 2, 4 tri-substituted aromatic compound or a 1, 2, 3 tri-substituted aromatic compound or mixtures thereof.

Also, preferably the ratio of the 1, 2, 4 tri-substituted aromatic to the 1, 2, 3 tri-substituted aromatic is at least 50:50. More preferably, the ratio is at least 80:20. Even more preferably, the ratio is at least 95:5. And, most preferably, the ratio is at least 98:2.

It has been reported in the literature that the isomerization and disproportionation of ortho-, meta- and para-xylene to para-xylene using a mixture of aluminum chloride and hydrogen chloride as catalyst results in the formation of some 1, 3, 5-trimethylbenzene in the product mixture. See Collins et al., Applied Catalysis, 7, (1983), 272-288. These authors also report that the 1, 3, 5-trimethylbenzene forms a pi-complex with aluminum chloride which results in a reduction in the catalytic activity of the aluminum chloride catalyst.

In view of this prior art, one would expect that during aromatic alkylation reactions with chloroaluminate ionic liquid catalysts (i.e. those ionic liquids which contain $AlCl_3$ as a catalyst component) that 1, 3, 5-trialkylbenzenes might form. Specifically during aromatic alkylation of xylenes using chloroaluminate ionic liquid catalysts, formation of 1, 3, 5-trimethylbenzene by disproportionation of xylene and isomerization of the resulting trimethylbenzene would be expected according to the prior art. As indicated in the prior art cited, one skilled in the art would be led to expect that under xylene alkylation conditions, a pi-complex with a 1, 3, 5-trialkybenzene could form and lead to catalyst deactivation.

By contrast, the present invention produced unexpected results when an aromatic compound, such as o-xylene, was alkylated with a mixture of olefins in the presence of an acidic ionic liquid, including chloroaluminate ionic liquid catalysts. Surprisingly, it has been discovered that alkylation of an aromatic compound, such as o-xylene, could be carried out using a mixture of olefins selected from olefins having a carbon range of from about $C_{12}$ to about $C_{30+}$ of normal alpha olefins under catalyst recycle conditions for a total production time of about 300 hours. Unlike the prior art, there was no evidence of a decrease in the reaction rate (i.e., no catalyst deactivation) with the process of the present invention.

Preparation of Alkylaromatic Sulfonate

In one embodiment of the present invention, the product prepared by the process described herein (i.e., alkylated orthoxylene: 1, 2, 4 trisubstituted alkylbenzene; 1, 2, 3 trisubstituted trisubstituted alkylbenzene and mixtures thereof) is further reacted to form a sulfonate.

Sulfonation

Sulfonation of the alkylaromatic, such as alkylorthoxylene, may then be performed in a manner by any method known to one of ordinary skill in the art. The sulfonation reaction is typically carried out in a continuous falling film tubular reactor maintained at about 55° C. The alkylorthoxylene is placed in the reactor along with the sulfur trioxide diluted with air, sulfiic acid, chlorosulfonic acid or sulfamic acid, thereby producing alkylorthoxylene sulfonic acid. Preferably, the alkylorthoxylene is sulfonated with sulfur trioxide diluted with air. The charge mole ratio of sulfur trioxide to alkylate is maintained at about 0.8 to 1.1:1.

Neutralization of Alkylaromatic Sulfonic Acid

Neutralization of the alkylaromatic sulfonic acid, such as alkylorthoxylene sulfonic acid, may be carried out in a continuous or batch process by any method known to a person skilled in the art to produce alkylaromatic sulfonates. Typically, an alkylaromatic sulfonic acid is neutralized with a source of alkali or alkaline earth metal. Preferably, the alklyaromatic sulfonic acid is neutralized with an alkaline earth metal hydroxide, such as but not limited to, calcium hydroxide or magnesium hydroxide.

Other embodiments will be obvious to those skilled in the art.

The following examples are presented to illustrate specific embodiments of this invention and are not to be construed in any way as limiting the scope of the invention.

EXAMPLES

Example 1

Preparation of Methyltributylammonium Chloroaluminate Ionic Liquid Catalyst

Anhydrous aluminum trichloride and methyltributylammonium chloride were dried overnight under vacuum at 100° C.

The preparation of the ionic liquid catalyst was carried out in a dry box. 550.6 grams of methyltributylammonium chloride was added to a beaker which was equipped with a magnetic stirring bar. 622.7 grams of anhydrous aluminum chloride was added to a second beaker. With the magnetic stirred activated, small portions of the solid aluminum chloride were slowly added to the beaker of methyltributylammonium chloride. As aluminum chloride was added, heat evolution took place and the reaction mixture began to turn "pasty" and then partially liquid. The rate of addition of aluminum chloride was slowed to moderate the temperature increase in the beaker. As more aluminum chloride was added, more liquid was formed and eventually the reaction mixture began to stir freely. After the addition entire amount of aluminum trichloride, the reaction mixture was allowed to cool to ambient temperature and was stirred overnight. The next morning the reaction mixture was filtered through a sintered glass filter which had been dried at 130 C. The final filtered ionic liquid catalyst was stored under nitrogen in a glass bottle.

Example 2

Ortho-Xylene Alkylation with C12-C30+ Normal Alpha Olefins

The aromatic alkylation of ortho-xylene (i.e., o-xylene) with a mixture of olefins was conducted in a process unit.

The alkylation feedstock consisted of a mixture of o-xylene and C12-C30+ normal alpha olefins with a molar ratio of xylene/olefin=5.0. The olefin used to make this feed was a commercial C12+ normal alpha olefin (nao) cut. The mixture of C12-C30+ nao comprised 79 wt % C12-C20 olefins and 4 wt % C32-C58 olefins. At the lowest boiling point, 20 wt % of the olefin was removed by distillation prior to making the alkylation feed mixture. The feed mixture was dried over 4A molecular sieves and stored under dry nitrogen during use. Because of the waxy nature of the alpha olefin, the alkylation feed mixture was heated to 50° C. with stirring to keep all the olefin in solution. O-Xylene was also dried over 4 A molecular sieves and stored under dry nitrogen during use.

A mixture of 300 mL of ionic liquid catalyst of Example 1 and 400 mL of o-xylene was prepared and was stored under dry nitrogen during use.

To start the catalytic run, o-xylene was pumped at a nominal rate of approximately 120 g/hour into the reactor, through the back pressure regulator into the liquid-liquid separator and finally into a hydrocarbon product reservoir. The reactor was stirred at 600 RPM and heated to 40° C. Pressure was increased by means of the back pressure regulator to about 50 psig. When temperature and pressure were lined out, the ionic liquid catalyst/o-xylene mixture was pumped into the reactor at a nominal rate of 20 grams per hour. At the same time, the o-xylene flow was stopped and the alkylation feed mixture was pumped into the reactor at approximately 120 g/hour. When sufficient catalyst built up in the bottom of the liquid-liquid separator and the catalyst recycle line leading to the inlet of the catalyst pump, the flow of fresh catalyst was stopped and the flow of recycled catalyst was started at the same nominal catalyst flow rate. This time marked the start of run.

During the run, product samples were collected in two ways. First, small samples were obtained periodically from a sample valve located in the line leading out from the back pressure regulator. Second, the bulk liquid product was collected in large product cans which were each changed at 12 hours of operation. Products were analyzed by gas chromatography and conversion was measured from the disappearance of olefin in the gas chromatograms of the products.

During the run, catalytic operation was occasionally stopped for maintenance on pumps or for addition of new containers of alkylation feed. Not including the time when the operation was temporarily stopped for maintenance, the unit operated to produce aromatic alkylate with a closed catalyst recycle loop for a total of 297 hours.

During the entire course of the run, all hydrocarbon product samples showed >99% olefin conversion, showing the robustness of the acidic ionic liquid catalyst under recycle conditions.

Example 3

Batch Ionic Liquid Alkylation of o-Xylene with $C_{12-30+}$ Normal Alpha Olefins To a dry, 3 liter, glass reactor fitted with a mechanical paddle stirrer, dropping funnel and reflux condenser under nitrogen was added 36.6 mL (about 42 grams or 0.12 moles) of ionic liquid made by reaction of one equivalent of trimethylammonium hydrochloride salt with two equivalents of aluminum chloride. To the ionic liquid at 22° C. was added dropwise a mixture of $C_{12-30+}$ normal alpha olefin (nao) dropwise over 18 minutes with stirring. The mixture of $C_{12}$-$C_{30+}$ nao comprised 75 wt % $C_{12}$-$C_{20}$nao and 5 wt % $C_{32}$-$C_{58}$ nao. The temperature of the reaction mixture increased to 78° C. The reaction was allowed to stir for an additional 2 hours at which time the temperature of the mixture had decreased to 24° C. The ionic liquid catalyst was separated from the reaction mixture in a separatory funnel and the organic layer was washed three time with cold water. The organic layer was then dried over anhydrous MgSO4, filtered and the unreacted o-Xylene removed by distillation under reduced pressure to afford a yellow liquid composed of approximately 1.6 wt % 3-Alkyl-o-Xylene (the 1, 2, 3, tri-substituted isomer) and 98.4 wt % 4-Alkyl-o-Xylene (the 1, 2, 4 tri-substituted isomer).

Example 4

Batch Ionic Liquid Alkylation of o-Xylene with $C_{14-30+}$ Normal Alpha Olefins In a dry, three neck 250 mL round bottom glass flask equipped with a mechanical stirrer, thermometer, water cooled condenser, liquid addition funnel under a blanket of dry nitrogen was added 5.1 grams of ionic liquid (approximately 10 millimoles Methyltributylammonium Chloroaluminate) followed by 20 grams (189 millimoles) of o-xylene. To this was added a mixture of 50 grams of $C_{14-30+}$ normal alpha olefins (nao) (approximately 186 millimoles) dissolved in 80 grams (755 millimoles) of o-Xylene dropwise over 15 minutes with stirring. The mixture of olefins comprised 71 wt % $C_{12}$-$C_{20}$ nao and 5 wt % $C_{32}$-$C_{58}$ nao. The temperature of the reaction mixture increased from 20° C. to 53° C. and was allowed to cool to 31° C. with stirring. The reaction mixture was transferred to a separatory funnel and the ionic liquid catalyst was separated from the organic mixture. The organic mixture was then washed twice with approximately 50 mL of water, dried over anhydrous $MgSO_4$, filtered and the excess o-Xylene was removed by distillation at reduced pressure on a rotoevaporator to afford a yellow oil composed of approximately 1.3 wt % 3-Alkyl-o-Xylene (the 1, 2, 3 tri-substituted isomer) and 98.7 wt % 4-Alkyl-o-Xylene (the 1, 2, 4 tri-substituted isomer).

Example 5

Sulfonation of $C_{12-30+}$ o-Xylene Alkylate

A $C_{12-30+}$ o-Xylene Alkylate, similar to that prepared in Examples 2, 3, and 4, above, was sulfonated by a concurrent stream of sulfur trioxide ($SO_3$) and air in a tubular reactor (approximately, 2 meters long, 1 cm inside diameter) in a down flow mode using the following conditions:

Reactor Temperature: 65° C.

Alkylate Feed Temperature: 65° C.

Air Flow: 192 L/hr $SO_2$ Flow: 18 L/hr

Alkylate Feed Flow: 4.6 grams/min

Charge Mole Ratio (alkylate:$SO_3$) 0.94:1

The $SO_3$ was generated by passing the mixture of oxygen and sulfur dioxide ($SO_2$) through a catalytic furnace containing vanadium oxide ($V_2O_5$).

Under these conditions, the crude $C_{12-30+}$ o-Xylene Sulfonic Acid produced had the following properties: 3.95 wt % Ca as Sulfonate and 0.82 wt % $H_2SO_4$.

It is understood that although modifications and variations of the invention can be made without departing from the spirit and scope thereof, only such limitations should be imposed as are indicated in the appended claims.

What is claimed is:

1. A process for preparing a synthetic petroleum sulfonate comprising
(a) reacting at least one aromatic compound with a mixture of olefins selected from olefins having from about 8 to about 100 carbon atoms, wherein the mixture of olefins contains a distribution of carbon atoms that comprise from about 4 percent to about 15 percent $C_{32}$ to $C_{58}$, in the presence of an acidic ionic liquid catalyst, wherein the resulting product comprises at least about 50 weight percent of a 1, 2, 4 tri-substituted aromatic compound or a 1, 2, 3 tri-substituted aromatic compound or mixtures thereof;

(b) reacting the product of (a) with sulfur trioxide, which has been diluted with air; and (c) neutralizing the product of (b) with an alkali or alkaline earth metal hydroxide.

2. The process according to claim 1 wherein the at least one aromatic compound is selected from unsubstituted aromatic compounds, monosubstituted aromatic compounds, and disubstituted aromatic compounds.

3. The process according to claim 2 wherein the unsubstituted aromatic compounds, monosubstituted aromatic compounds, and disubstituted aromatic compounds are selected from benzene, toluene, meta-ylene, para-xylene, ortho-xylene, and mixtures thereof.

4. The process according to claim 3 wherein the at least disubstituted aromatic compound is selected from meta-xylene, para-xylene, ortho-xylene and mixtures thereof.

5. The process according to claim 4 wherein the at least one disubstituted aromatic compound is ortho-xylene.

6. The process according to claim 5 wherein the mixture of olefins is a mixture of linear olefins, a mixture of linear isomerized olefins, a mixture of branched olefins, a mixture of partially branched olefins or a mixture thereof.

7. The process according to claim 6 wherein the mixture of olefins is a mixture of linear olefins.

8. The process according to claim 7 wherein the mixture of linear olefins is a mixture of normal alpha olefins.

9. The process according to claim 8 wherein the mixture of linear olefins comprises olefins derived through cracking of petroleum wax or Fischer Tropsch wax.

10. The process according to claim 9 wherein the Fischer Tropsch wax is hydrotreated before cracking.

11. The process according to claim 6 wherein the mixture of olefins is derived from linear alpha olefins or isomerized olefins containing from about 8 to 100 carbon atoms.

12. The process according to claim 11 wherein the mixture of olefins is derived from linear alpha olefins or isomerized olefins containing from about 10 to about 80 carbon atoms.

13. The process according to claim 12 wherein the mixture of olefins is derived from linear alpha olefins or an isomerized olefins containing from about 14 to about 60 carbon atoms.

14. The process according to claim 7 wherein the mixture of linear olefins is a mixture of linear internal olefins which have been derived from olefin metathesis.

15. The process according to claim 1 wherein the mixture of olefins is a mixture of branched olefins.

16. The process according to claim 15 wherein the mixture of branched olefins comprises polyolefin compounds derived from $C_3$ or higher monoolefins.

17. The process according to claim 16 wherein the polyolefin compound is either polypropylene or polybutylene.

18. The process according to claim 17 wherein the polyolefin compound is polypropylene.

19. The process according to claim 18 wherein the polyolefin compound is polybutylene.

20. The process according to claim 1 wherein the acidic ionic liquid catalyst comprises a first component and a second component, said first component comprising a compound selected from the group consisting of aluminum halide, alkyl aluminum halide, gallium halide, and alkyl gallium halide, and said second component comprising a salt selected from an ammonium salt, a phosphonium salt, or a sulfonium salt.

21. The process according to claim 20 wherein the first component is aluminum halide or alkyl aluminum halide.

22. The process according to claim 21 wherein the first component is aluminum trichloride.

23. The process according to claim 22 wherein said second component is selected from one or more of a hydrocarbyl substituted ammonium halide, hydrocarbyl substituted imidazolium halide, hydrocarbyl substituted pyridinium halide, alkylene substituted pyridinium dihalide, or hydrocarbyl substituted phophonium halide.

24. The process according to claim 23 wherein the second component is an alkyl substituted ammonium halide containing one or more alkyl moieties having from about 1 to about 9 carbon atoms.

25. The process according to claim 24 wherein the second component comprises at least trimethyl amine hydrochloride.

26. The process according to claim 25 wherein the second component is an alkyl substituted imidazolium halide.

27. The process according to claim 26 wherein the second component comprises at least 1-ethyl-3-methyl-imidazolium chloride.

28. The process according to claim 27 wherein the acidic ionic liquid catalyst is recycled.

29. The process according to claim 1 wherein the reaction takes place in a continuous process.

* * * * *